United States Patent [19]

Hama et al.

[11] Patent Number: 4,680,969

[45] Date of Patent: Jul. 21, 1987

[54] ULTRASONIC PROBE JIG

[75] Inventors: Yasuo Hama; Shigetake Takaku, both of Mobara, Japan

[73] Assignee: Hitachi, Ltd., Tokyo, Japan

[21] Appl. No.: 892,338

[22] Filed: Aug. 1, 1986

[30] Foreign Application Priority Data

Sep. 6, 1985 [JP] Japan ................... 60-195812

[51] Int. Cl.$^4$ ............................................ G01N 29/04
[52] U.S. Cl. ............................................... 73/661
[58] Field of Search ............................. 73/661, 634

[56] References Cited

U.S. PATENT DOCUMENTS 4,016,752  4/1977  Carey ........................................ 73/661
4,367,650  1/1983  Hilgner et al. ........................... 73/661

*Primary Examiner*—Anthony V. Ciarlante
*Attorney, Agent, or Firm*—Charles E. Pfund

[57] ABSTRACT

An ultrasonic probe jig includes a leaf spring, a support member, a mounting mechanism, and a regulating member. The leaf spring member is brought into contact with the upper surface of an ultrasonic probe to be located on an object to be examined. The support member supports a peripheral portion of the leaf spring member. The mounting mechanism pivotally mounts a support rod coupled to a control device on the support member. One end of the regulating member is mounted to the support rod and the other end thereof is engaged with the support member. The regulating member regulates pivotal movement of the support member.

8 Claims, 9 Drawing Figures

ULTRASONIC PROBE JIG

BACKGROUND OF THE INVENTION

The present invention relates to an ultrasonic probe jig for bringing an ultrasonic jig into contact with a surface of an object to be examined, so as to perform efficient ultrasonic transmission and reception.

It is generally important for an ultrasonic flaw or thickness detection probe to effectively emit an ultrasonic beam into the object and effectively detect an echo wave from the interior of the object.

A probe 1 comprises a rectangular prism or a cylinder shown in FIG. 1. An ultrasonic generation or detection surface of a conventional ultrasonic generation or detection element (e.g., a magnetostrictive element, or an electric-mechanical vibration conversion system using an electrostrictive or piezoelectric element) is mounted at the lower end portion of the probe. This surface is brought into tight contact with and parallel to the surface of an object 2. The probe is then pressed at an optimal pressure.

In conventional ultrasonic inspection, an operator presses the probe on the surface of the object by his hand. However, manual pressure control is very difficult and errors often occur.

SUMMARY OF THE INVENTION

It is, therefore, a principal object of the present invention to provide an ultrasonic probe jig which eliminates errors occurring when an operator manually presses a conventional ultrasonic probe onto a surface of an object to be measured, and which mechanically and automatically brings the probe into contact with the object during ultrasonic flaw detection or ultrasonic measurements.

In order to achieve the above object of the present invention, there is provided an ultrasonic probe jig comprising: a leaf spring member brought into contact with an upper surface of an ultrasonic probe to be located on an object to be examined; a support member for supporting a peripheral portion of the leaf spring member; a mounting mechanism for pivotally mounting a support rod coupled to a control device on the support member; and a regulating member one end of which is mounted to the support rod and the other end of which is engaged with the support member, the regulating member being adapted to regulate pivotal movement of the support member.

DESCRIPTION OF THE PREFERRED EMBODIMENTS

Figure 1:
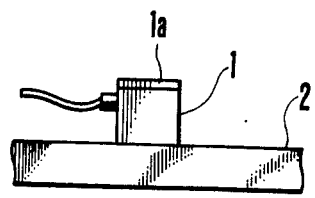
FIG. 1 is a side view showing a conventional probe.
Figure 2A:
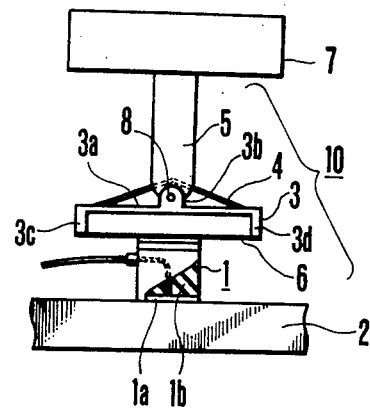
FIGS. 2A and 2B are respectively a side view and a plan view of an ultrasonic probe jig according to an embodiment of the present invention.
Figure 2B:
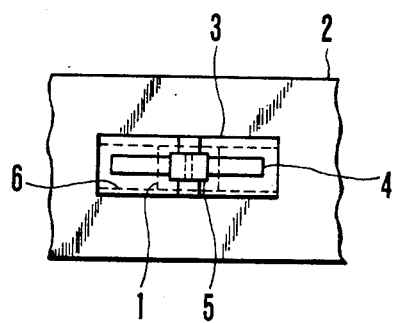

FIGS. 2A and 2B show an ultrasonic probe jig according to an embodiment of the present invention.

Referring to FIGS. 2A and 2B, a jig 10 as the main feature of the present invention is mounted on an ultrasonic probe 1 to be brought into contact with an object 2 to be examined. The jig 10 has a C-shaped arm 3 when viewed from its side. A proximal portion 3a of the arm 3 is flat. A pair of projections 3b are formed at substantially the central portion of the proximal portion 3a along the longitudinal direction thereof and are spaced apart from each other along the direction of width of the proximal portion 3a. A shaft 8 connects the projections 3b. The arm 3 is pivotally engaged by the shaft 8 with the distal end of a support rod 5 coupled to a control device 7. A leaf spring or flexible member 6 is hooked between both ends 3c and 3d of the arm 3. The leaf spring 6 is adapted to be brought into contact with the top of the probe 1. An inverted V-shaped spring 4 is engaged with the flat proximal portion 3a. The central portion of the spring 4 is locked by the support rod 5. The spring 4 applies the restoration force to the arm 3 upon pivotal movement of the arm 3 about the shaft 8. In this case, the leaf spring 6 having a smaller width than that of the arm 3 has torsion flexibility around the longitudinal direction of the arm 3. A resonator plate 1a made of quartz or for efficiently generating an ultrasonic wave is mounted on the lower end face of the probe 1 in a known manner. A damper 1b made of epoxy resin reinforced with Bakelite or tungsten is in contact with the rear surface of the resonator plate 1a. With the above arrangement, the probe 1 is mounted elastically (i.e., with a restoration force) on a freely inclining surface along the entire circumference of the support rod 5 such that the probe 1 can be elastically movable in a direction perpendicular to the freely inclining surface (i.e., so as to optimize a contact pressure in cooperation with a force for urging the support rod 5). The spring 4 causes the resonator surface to restore a position substantially parallel to the surface of the object 2 upon separation of the probe 1 from the surface of the object while the probe 1 can be inclined with respect to the support rod 5. The spring 4 may be formed of a plate or a rod. The spring 4 may also be a coil spring. In this case, both ends of the spring 4 are fixed to the arm 3.

The support rod 5 is coupled to a carrier mechanism (not shown) for bringing the probe 1 and the entire jig including the support rod 5 and a flexible support member into contact with or separating it from the surface of the object 2. Although the moving direction of the carrier mechanism is preferably perpendicular to the surface of the object 2, the moving direction cannot always be set in such a manner. The moving direction or the like must be taken into consideration when the flexible member structure is selected.

FIGS. 3A and 3B and FIGS. 4A and 4B show other embodiments of ultrasonic probe jigs. The same reference numerals as in FIGS. 2A and 2B denote the same parts in FIGS. 3A and 3B and FIGS. 4A and 4B.

Figure 3A:
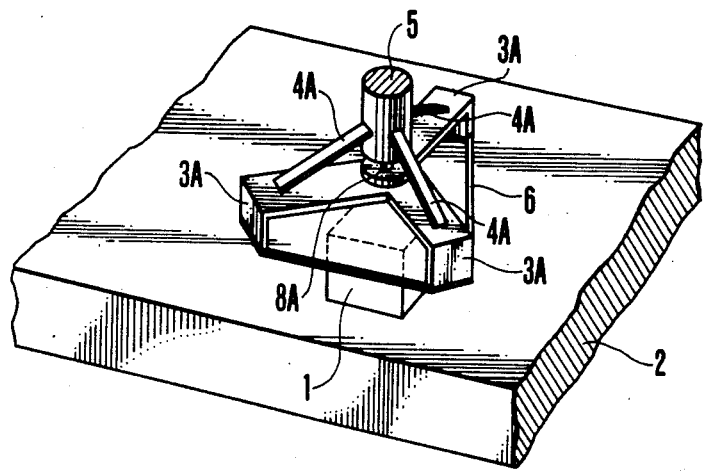
FIGS. 3A and 3B are respectively a side view and a perspective view of an ultrasonic probe jig according to another embodiment of the present invention.
Figure 3B:
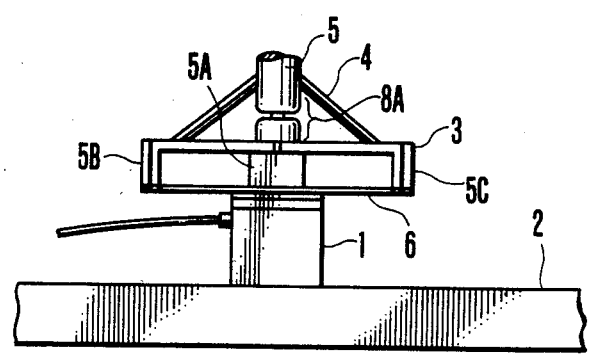

Referring to FIGS. 3A and 3B, a leaf spring 6 contacting a probe 1 is supported by support plates 3A. The support plates 3A extend at three equal angular positions, and the distal ends of the support plates 3A are bent downward. A pivot mechanism 8A is coupled to a common connecting portion of the support plates 3A. A support rod 5 is pivotal about the pivot mechanism 8A. Reference numerals 4A denote springs extending from the support rod 5 to the flat portions of the support plates 3A to regulate pivotal movement of the support plates 3A.

Figure 4A:
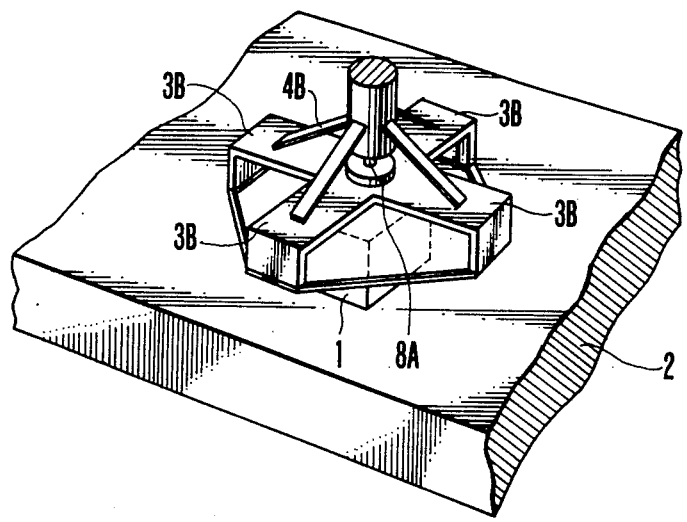
FIGS. 4A and 4B are respectively a side view and a perspective view of an ultrasonic probe jig according to still another embodiment of the present invention.
Figure 4B:
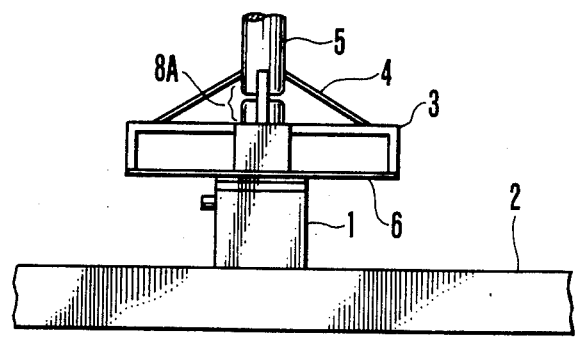

Referring to FIGS. 4A and 4B, support plates 3B extend at four equal angular positions and their distal ends are bent downared. A leaf spring 6 is supported by the support plates 3B. Springs 4B extend from the support rod 5 to the corresponding support plates 3B. Other arrangements of the jig in FIGS. 4A and 4B are the same as those in FIGS. 3A and 3B.

Figure 5:
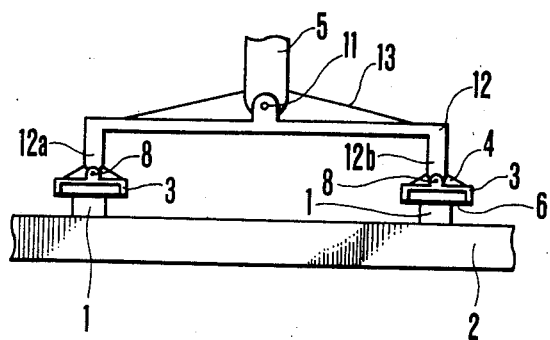
FIGS. 5 and 6 are respectively side views showing a probe support structure when two probes are used.
Figure 6:
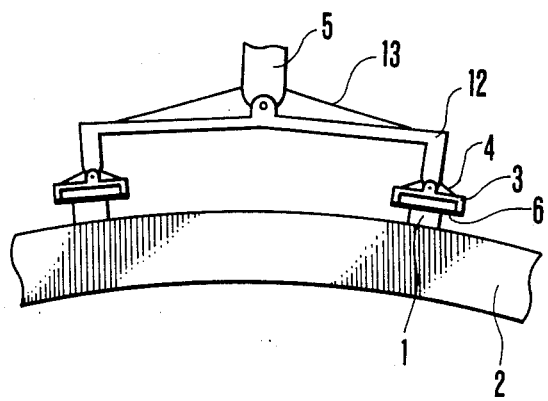

In the above embodiments, only one probe is used to generate and detect the ultrasonic beam. However, a plurality of probes, especially, two probes are often used. In this case, each of the two probes generates and detects the ultrasonic beam to simultaneously detect two portions. Alternatively, one probe is used as a transmission probe and the other one is used as a reception probe. An arrangement with two probes is illustrated in FIGS. 5 and 6. Referring to FIGS. 5 and 6, a C-shaped support member 12 (when viewed from the side at which a shaft 11 is engaged with a support rod 5) is used. The same jigs 10 as in FIGS. 2A and 2B are mounted at both ends of the support member. Both ends 12a and 12b of the support member 12 correspond to the support rod 5 in FIGS. 2A and 2B. Arms 3 are respectively coupled to the ends 12a and 12b through shafts. Leaf springs 6 and springs 4 mounted in association with the arms 3 are the same as those in FIGS. 2A and 2B. The proximal end 12a of the support member 12 is flat and an inverted V-shaped spring 13 is mounted on the flat proximal portion. The central portion of the spring 13 is fixed to the support rod 5. The spring 13 supplies a restoration force to the support member 12 upon pivotal movement of the support member 12 about the support rod 5. Probes 1 are mounted at both ends of the support member 7 elastically and rotatably supported at an end of one support rod 5 through jigs 10 shown in FIGS. 2A and 2B. In particular, since the surface of the object 2 is curved in FIG. 6, the shape of the support member 12 follows the surface shape of the object 2.

A step may be formed between two or more portions to be examined, or the surfaces of portions to be examined may be inclined in different directions. In order to simultaneously bring the probes into tight contact with these portions, the shape of the support member may be altered according to the surface shape of the object to be examined, in the same manner as in FIG. 6. The contact pressures between the probes and the object portions to be measured cannot always be optimized (for example, the objects to be examined must have the identical dimensions, but errors occur during the fabrication), the purpose described above can be substantially achieved.

According to the present invention as described above, the ultrasonic generation or detection surface at the lower end of the probe is brought into tight contact with and parallel to the surface of the object to be examined at an optimal pressure. The measuring errors can be minimized, and ultrasonic testing and inspection can be mechanically and automatically performed. In addition, the jig according to the present invention has a simple structure, thus requiring simple maintenance.

The present invention is not limited to the particular embodiments described above. Various changes and modifications may be made within the spirit and scope of the invention. For example, the peripheral portion of the leaf spring brought into contact with the upper surface of the probe may be supported by a support member, and the support member may be pivotal about a support rod.

What is claimed is:
1. An ultrasonic probe jig comprising:
   a leaf spring member brought into contact with an upper surface of an ultrasonic probe to be located on an object to be examined;
   a support member for supporting a peripheral portion of said leaf spring member;
   a mounting mechanism for pivotally mounting a support rod coupled to a control device on said support member; and
   a regulating member one end of which is mounted to said support rod and the other end of which is engaged with said support member, said regulating member being adapted to regulate pivotal movement of said support member.

2. A jig according to claim 1, wherein said support member comprises an arm, a central portion of which is constituted by a flat portion and distal portions of which are bent downward.

3. A jig according to claim 2, wherein a pivot mechanism is mounted on said central portion of said arm to pivotally support said support rod.

4. A jig according to claim 2, wherein the other end of said support member is locked on the flat portion of said arm.

5. A jig according to claim 1, wherein said support member comprises arms having flat portions extending at three equal angular positions and distal portions bent downward.

6. A jig according to claim 1, wherein said support member comprises arms having flat portions extending at four equal angular positions and distal portions bent downward.

7. An ultrasonic jig assembly comprising:
   a support rod member;
   supporting means pivotally supported by said support rod member; and
   ultrasonic jigs, each comprising a leaf spring member brought into contact with an upper surface of an ultrasonic probe to be located on an object to be examined, a support member for supporting a peripheral portion of said leaf spring member, a mounting mechanism for pivotally mounting a support rod coupled to a control device on said support member, and a regulating member one end of which is mounted to said support rod and the other end of which is engaged with said support member, said regulating member being adapted to regulate pivotal movement of said support member,
   said ultrasonic jigs being pivotally mounted at both ends of said supporting means.

8. An assembly according to claim 7, wherein said supporting means is bent according to an arcuated shape of the object to be examined.

* * * * *